United States Patent [19]

Szur

[11] 4,140,709
[45] Feb. 20, 1979

[54] ANIONIC FLUOROCHEMICAL SURFACTANTS

[75] Inventor: Alex J. Szur, North Plainfield, N.J.

[73] Assignee: Diamond Shamrock Corporation, Cleveland, Ohio

[21] Appl. No.: 560,719

[22] Filed: Mar. 21, 1975

[51] Int. Cl.$^2$ ............................................. C07C 141/02
[52] U.S. Cl. ............................ 260/458 F; 260/30.8 R; 568/677
[58] Field of Search ........................ 260/458 F, 615 F

[56] References Cited

U.S. PATENT DOCUMENTS

| | | | |
|---|---|---|---|
| 3,514,487 | 5/1970 | Anello et al. | 260/458 F |
| 3,527,742 | 9/1970 | Pittman et al. | 260/615 F |
| 3,651,120 | 3/1972 | Anello et al. | 260/458 F |
| 3,657,306 | 4/1972 | Murray | 260/458 F |
| 3,706,773 | 12/1972 | Anello et al. | 260/458 F |

Primary Examiner—Nicky Chan
Attorney, Agent, or Firm—Neal T. Levin; Leslie G. Nunn, Jr.

[57] ABSTRACT

6-Hydroxyhexyl perfluoroisopropyl ether is prepared by reaction of hexafluoroacetone and potassium fluoride to obtain an alcoholate which is then reacted with 1-chloro-6-hexanol. One mole of the ether may be reacted with about 1 mole to about 20 moles of ethylene oxide to produce a hydroxyethyl ether. One mole of 2,2,3,4,4,4-hexafluorobutanol may be reacted with from about 1 to about 5 moles of propylene oxide to produce a hydroxypropyl ether. One mole of hexafluorobutanol may also be reacted with about 1 to about 5 moles of propylene oxide and then about 1 mole to about 20 moles of ethylene oxide to produce a hydroxyethyl ether. The hydroxyhexyl ether, hydroxylpropyl ether and both hydroxyethyl ethers may be sulfated to produce anionic surfactants which are useful as antistatic agents and lubricants for polymeric shapes such as nylon films and filaments.

9 Claims, No Drawings

ANIONIC FLUOROCHEMICAL SURFACTANTS

BACKGROUND OF THE INVENTION

1. Field of the Invention

This invention relates to anionic fluorochemical surfactants useful as antistatic agents and lubricants for polymeric shapes.

2. Description of the Prior Art

U.S. Pat. No. 3,702,870 — Pittman et al., issued Nov. 14, 1972, and U.S. Pat. No. 3,758,538 — Litt et al., issued Sept. 11, 1973, describe preparation of fluorinated alcoholates by reaction of a fluoroketone with an alkali metal fluoride. In Pittman et al., the alcoholates are then reacted with acyl halides to obtain esters useful in improving water-repellency and oil-repellency of textiles. In Litt, et al., the alcoholates are then reacted with olefins to obtain fluorine containing ethers useful as surfactants.

U.S. Pat. No. 2,723,999 — Cowen et al., issued Nov. 15, 1955, describes preparation of a hydroxyethyl terminated ether by reaction of fluorinated alcohol with ethylene oxide.

U.S. Pat. No. 3,282,012 — Day, issued Nov. 1, 1966, describes the sulfation of 2-perfluoroalkylethanol.

Although these patents teach preparation of fluorinated surfactants, there is a definite need for improved fluorinated surfactants having useful properties as antistatic agents and lubricants for polymeric shapes.

STATEMENT OF THE INVENTION

Fluorochemical anionic surfactants are prepared:

(A) by reaction of hexafluoroacetone and potassium fluoride to obtain an alcoholate, potassium heptafluoroisopropoxide, which is then reacted with 1-chloro-6-hexanol to obtain 6-hydroxyhexyl perfluoroisopropyl ether which is then sulfated, (B) by reaction of hexafluoroacetone and potassium fluoride to obtain an alcoholate, potassium heptafluoroisopropoxide, which is then reacted with 1-chloro-6-hexanol to obtain 6-hydroxyhexyl perfluoroisopropyl ether which is then reacted with ethylene oxide and then sulfated, and (C) by reaction of 2,2,3,4,4,4-hexafluorobutanol with propylene oxide, then with ethylene oxide and thereafter sulfated to obtain useful anionic fluorochemical surfactants. These surfactants include the sulfates of the reaction product of 6-hydroxyhexyl perfluoroisopropyl ether with from about 1 to about 20 moles of ethylene oxide and the reaction product of hexafluorobutanol with from about 1 to about 5 moles of propylene oxide and with from about 1 to about 20 moles of ethylene oxide. These anionic surfactants are useful as antistatic agents, lubricants and antisoiling agents for polymeric shapes such as nylon films and filaments.

DESCRIPTION OF THE PREFERRED EMBODIMENTS

The fluorochemical surfactants of the present invention are anionic surfactants derived from two commercial fluorochemicals; hexafluoroacetone and 2,2,3,4,4,4-hexafluorobutanol.

Several synthetic routes are available to extend the hydrophobic chain of these two starting materials and to introduce the desired hydrophilic functionality required in surfactants. For example, the acetone may be reacted with potassium fluoride in diglyme to obtain the alcoholate, potassium heptafluoroisopropoxide shown in Reaction (I).

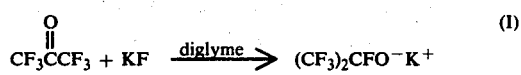

Then the alcoholate may be reacted with 1-chloro-6-hexanol to obtain ether-alcohol as shown in Equation (II).

Likewise, 2,2,3,4,4,4-hexafluorobutanol may be reacted with propylene oxide (PO) to obtain the polyethers shown in Equation (III).

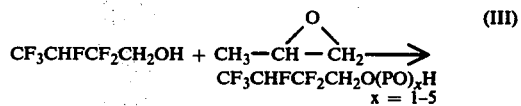

Further, the ether-alcohol reaction product of Equation (II) may be ethoxylated with ethylene oxide (EO) to obtain the ethoxylates shown in Equation (IV).

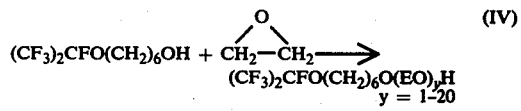

and similarly the propoxylated reaction products of Equation (III) may be reacted with ethylene oxide to obtain the ethoxylates shown in Equation (V).

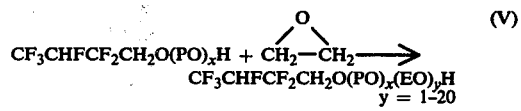

Anionic hydrophilic functionality may be introduced into the ether-alcohol reaction product of Equation (II) using chlorosulfonic acid or sulfamic acid as the sulfating agent in the reactions shown in Equation (VI).

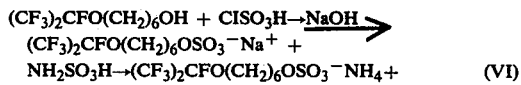

Likewise, anionic functionality may be introduced into the propoxylate reaction product of Equation (III) by the reaction shown in Equation (VII).

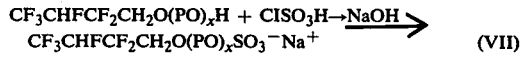

Equimolar or approximately equimolar quantities of reactants may be employed in Reactions (I) through (VII) other than in those reactions where ethylene oxide and propylene oxide are employed and the quantities of ethylene oxide and propylene oxide are indicated.

Sulfating agents such as sulfuric acid, oleum, sulfur trioxide, sulfamic acid, chlorosulfonic acid or the like may be used. Sulfating reaction temperatures will vary from 0° C. or lower to 150° C. or higher depending on the particular sulfating agent used. Equimolar quantities of the reaction product and sulfating agent are preferred. However, it may be desirable to use 10% less or more of the sulfating agent in some instances. It is to be understood that the chemistry of these sulfating agents are well understood and that choice of the reaction temperature and other conditions are within the skill of the art.

Antistatic properties of treated polymeric shapes such as fibers, filaments, foils or films containing from about 0.1% to about 5% by weight of one of the above surfactants based on the weight of the shape may be determined using the procedure described by M. J. Schick in Friction and Lubrication of Synthetic Fibers, Part I, Textile Research Journal, Vol. 43, No. 2, pp 103–109 (February 1973). In this procedure, a given charge is placed on a polymeric shape such as a yarn specimen and the time required for one-half of the charge on the shape to dissipate from the shape is measured and recorded as the antistatic half-life.

Lubricity properties of shapes treated with one of the above surfactants may be determined by the procedure given in the above mentioned publication or by the procedure using the tripod sled apparatus as described by M. J. Schick, T. F. MacDonnell and J. H. Nash in Wear 25, (1973) pp 385–392. Both procedures are described in greater detail in the examples below.

Further, tendency of these surfactants to improve antisoiling properties of shapes such as carpeting may be evaluated by the procedure described in the examples.

The surfactant may be applied directly to the polymeric shape by any known method such as by means of a spray, by means of a bath, by means of an aqueous solution or dispersion or by means of a solvent such as a solution of the surfactant in a solvent such as chlorinated hydrocarbon, water or the like. If desired, the surfactant may be applied in solvent free form. Likewise, the surfactant may be compounded with the polymeric material prior to forming the filament, fiber, film, foil or the like. These application methods are well known in the art.

The surfactants of this invention may be used to treat various materials having any of the aforesaid shapes or structures. Such materials include natural, man-made and synthetic fibers such as cotton, wool, silk, jute, sisal, hemp, fur, flax, kapok, rayon, cellulose acetate, cellulose triacetate, polyamides such as nylon, polyesters such as polyethylene terephthalate (Dacron), acrylics such as polyacrylonitrile, vinyl resins such as copolymers of polyvinyl chloride and polyvinyl acetate, copolymers of vinylidene chloride and vinyl chloride, copolymers of acrylonitrile and vinyl chloride, or the like, polystyrene, polyethylene, polypropylene, polyurethane, glass, ceramic, asbestos, protein fibers such as vicara and peanut protein, blends of these and the like. Blends of several fibers may be used. The term fiber includes textile materials in the form of fibers, continuous or spun yarns, filaments, rovings, slivers, tops and the like.

For a fuller understanding of the nature and objects of this invention, reference may be made to the following examples which are given merely to illustrate the invention and are not to be construed in a limiting sense. All weights, proportions and percentages are on a weight basis unless otherwise indicated. Likewise, all temperatures are ° C. unless otherwise indicated.

EXAMPLE I

This example describes the preparation of the ammonium and sodium sulfates of 6-hydroxyhexyl perfluoroisopropyl ether.

6-Hydroxyhexyl perfluoroisopropyl ether

A 1 l., four-necked flask, fitted with a stirrer, thermometer, gas inlet tube, addition funnel and dry ice condenser, was purged with nitrogen and charged with 200 ml of diglyme and 21.3 g (0.37 m) of potassium fluoride. The slurry was cooled to $-40°$ C. in an isopropanol-dry ice bath and 66 g (0.4 m) of hexafluoroacetone added over a period of 45 minutes. After the addition was completed, the reaction mixture was allowed to warm to room temperature and became a clear solution of potassium perfluoroisopropoxide.

1-Chloro-6-hexanol (50 g, 0.37 m) was added allowing the exotherm to raise the temperature to 36° C. After the addition was completed, the reaction mixture was heated at 40° C. for 2 hours. The reaction mixture was washed with a sodium chloride solution and vacuum distilled to yield 28 g of clear, colorless liquid 6-hydroxyhexyl perfluoroisopropyl ether b.p. 119°–122° C./18 mm, $n_d^{21.5}$ 1.4278. IR analysis showed the following major absorption bands: 3400, 2940, 2862, 1220, 1090 cm$^{-1}$.

6-Hydroxyhexyl perfluoroisopropyl ether sodium sulfate

A 100 ml four-necked flask fitted with a stirrer, thermometer, addition funnel and gas inlet was charged with 24.1 g (0.08 m) of 6-hydroxyhexyl perfluoroisopropyl ether, cooled under nitrogen to 15° C. and held for one half hour. Chlorosulfonic acid (10.3 g, 0.08 m) was added over a period of 30 minutes with stirring while maintaining the temperature at 15°–20° C., reaction was quite exothermic. Stirring was continued for one hour when the addition was completed. The reaction mixture was poured into a solution of 6.9 g of 50% sodium hydroxide in 68 g of cold water. The resulting solution was clear and colorless containing 27.2% by weight of 6-hydroxy perfluoroisopropyl ether sodium sulfate and was designated as Product I (A).

6-Hydroxyhexyl perfluoroisopropyl ether ammonium sulfate

6-Hydroxyhexyl perfluoroisopropyl ether (15.5 g, 0.05 m) and sulfamic acid (5.1 g, 0.05 m) were combined and heated with stirring at 145° for one hour. Hexane (25 ml) was added to the cooled reaction mixture to remove unreacted alcohol. Filtration and vacuum drying gave a brown soft solid product, 6-hydroxyhexyl perfluoroisopropyl ether ammonium sulfate which was designated as Product I (B). IR analysis showed the following major absorption bands: 3200, 2935, 2860, 1430, 1210 cm$^{-1}$.

EXAMPLE II

This example describes preparation of the sodium sulfate of the four mole propoxylate of 2,2,3,4,4,4-hexafluorobutanol.

2,2,3,4,4,4-Hexafluorobutanol plus 4 moles of propylene oxide

To a 250 ml four-necked flask fitted with a stirrer, thermometer, addition funnel and dry ice condenser was charged 50 g (0.27 m) of 2,2,3,4,4,4-hexafluorobutanol and 0.2 g of boron trifluoride etherate solution. The reaction flask was purged with nitrogen at room temperature and then heated to 40° C. Propylene oxide (51 g, 0.88 m) was added slowly from the addition funnel while maintaining the temperature at 40° C. Stirring was continued after the addition was completed until the exotherm subsided. The reaction mixture was stripped under vacuum 50° C./10 mm yielding the 4 mole propoxylate of 2,2,3,4,4,4-hexafluorobutanol with a hydroxyl number of 135.9 calc for 4 mole propoxylate 135.5.

Sodium Sulfate of the 4 mole propoxylate of 2,2,3,4,4,4-Hexafluorobutanol

A 250 ml four-necked flask fitted with a stirrer, thermometer, addition funnel and gas inlet was charged with 58.6 g (0.14 m) of the 4 mole propoxylate of 2,2,3,4,4,4-hexafluorobutanol and cooled under nitrogen to 15° C. and held for one half hour. Chlorosulfonic acid (17.4 g, 0.15 m) was added over a thirty minute period with stirring while maintaining the temperature at 15°-20° C. Stirring was continued for one hour when the addition was completed. The reaction mixture was poured into a solution of 11.7 g of 50% sodium hydroxide in 157 g of cold water. The resulting solution was clear and light yellow containing 26.6% by weight of product, designated as Product II (A).

EXAMPLE III

Lubricating properties of the above fluorochemical surfactants, I (A), I (B) and II (A), were determined using the following procedure. Coefficient of friction of each surfactant was measured using a Rothschild F-Meter 1081 for Measuring Coefficients of Friction (formerly Haberline, Inc., Raleigh, N.C., now Lawson-Hemphill Sales, Inc., Spartanburg, S.C.) with two Rothschild Electronic Tensiometers (formerly Haberline, Inc., Raleigh, N.C., now Lawson-Hemphill Sales, Inc., Spartanburg, S.C.), as described by M. J. Schick in Friction and Lubrication of Synthetic Fibers, Part I, Textile Research Journal, Vol. 43, No. 2, pp. 103-109 (February 1973). The surfactant was applied at 1% by weight based on the weight of fiber to the fiber and the treated fiber conditioned for 24 hours at 50% relative humidity and 72° F. The coefficient of friction of the conditioned fiber was then measured using the apparatus described above in the following procedure.

An aqueous or isopropanol solution or dispersion of each surfactant was applied to a sample of 200/34 nylon filament yarn. Each yarn sample was then dried to remove water or alcohol and conditioned for 24 hours at 50% relative humidity and 72° F. The conditioned, treated yarn sample, which contained 1% by weight of the surfactant based on the weight of the fiber, was then evaluated to determine the fiber to metal coefficient of friction at 50% relative humidity and 72° F. Coefficients of fiber to metal friction were measured using the Rothschild F-Meter 1081 with two Rothschild Electronic Tensiometers. Incoming tension on the yarn was 0.5 g per denier and the friction surface was a 0.5 inch diameter chrome pin having a roughness value of 52 RMS. Yarn was wrapped around the pin circumference once. Yarn speeds were: 5.5, 55, 100 and 300 yards per min. Results of these friction tests are shown in Table I below.

Antistatic properties of the conditioned, treated yarn samples were also determined. The antistatic half-life test used in these measurements is the test described in the above publication. In this test, a given charge is placed on a yarn specimen and the time required for one half of the charge on the specimen to dissipate from the test specimen is measured and recorded as the antistatic half-life of the treated fiber. Results of these tests are shown as the Antistatic Half-Life Seconds in Table I below.

TABLE I
COEFFICIENTS OF FRICTION AND ANTI-STATIC PROPERTIES[1]

| Product | Speed (yds/min) | Coefficient of fiber to metal friction | Anti-static Half-Life Seconds |
|---|---|---|---|
| Butyl Stearate | 5.5 | 0.160 | 36,000 |
|  | 55 | 0.160 |  |
|  | 100 | 0.173 |  |
|  | 300 | 0.186 |  |
| I (A) | 5.5 | 0.283 | 850 |
|  | 55 | 0.435 |  |
|  | 100 | 0.442 |  |
|  | 300 | 0.454 |  |
| I (B) | 5.5 | 0.270 | 0.88 |
|  | 55 | 0.475 | — |
|  | 100 | 0.540 |  |
| II (A) | 5.5 | 0.394 | 28.56 |
|  | 55 | 0.475 |  |
|  | 100 | 0.528 |  |
|  | 300 | 0.518 |  |

[1]1% on nylon 200 DuPont at 72° F, 50% humidity, 1 loop on chrome pin.

EXAMPLE IV

Each of the above fluorochemical surfactants, Product of I (A), I (B) and II (A), was applied to the surface of nylon 66 film at a concentration of about 1% by weight of surfactant based on weight of the film. Each sample conditioned for one week at 50% relative humidity and 72° F. prior to testing and then tested under these conditions. Frictional properties were determined by the procedure using the tripod sled apparatus described by M. J. Schick, T. F. MacDonnell and J. H. Nash in Wear 25, (1973) pp 385-392 to determine the coefficient of friction for film to metal boundary lubrication at a relative surface speed of 8 inches per minute and at three loads: 300 g, 600 g and 900 g. Frictional force was measured using a Statham Transducer (Statham Medical Instrument, Inc., Hato Rey, Puerto Rico) and recorded on a Sanborn Recorder 150 equipped with a carrier preamplifier (Hewlett Packard Co., Palo Alto, Calif.). The coefficient of friction, f=F/W where f signifies the frictional coefficient, F the frictional force and W the normal load, was then calculated from the average measured force divided by the load. A blank sample was also tested by the same procedure. Results of these tests are shown in Table II. These results show that the coefficient of friction when Product I (A), I (B) or II (A) was applied, was considerably lower than the blank sample.

TABLE II
COEFFICIENTS OF FRICTION (METAL-NYLON), TRIPOD SLED

| | Coefficient of Friction | | |
|---|---|---|---|
| Product of Example | 300 gms. | 600 gms. | 900 gms. |
| Blank | 0.16 | 0.16 | 0.13 |
| I (A) | 0.02-0.08 | 0.05-0.09 | 0.02-0.06 |
| I (B) | 0.1-0.15 | 0.08-0.12 | 0.13 |
| II (A) | 0.02 | 0.03 | 0.03 |

EXAMPLE V

In the carpet soiling test, the relative tendency of carpet samples to retain soil was measured by application of about 2 g of a synthetic soil containing

| Ingredient | % By Weight |
|---|---|
| Michigan peat | 42.75 |
| Cement | 17.00 |
| Silica | 17.00 |
| Koalin | 17.00 |
| Mineral Oil | 4.00 |
| Carbon Black | 1.75 |
| Red Iron Oxide | 0.50 |

The soil was prepared by pebble milling the above ingredients for 35 hours and then drying the mixture at 100° C. for five hours. To avoid variations, sufficient soil was prepared to complete a series of soiling tests.

The soil was applied to the carpet samples using a can having both ends removed, measuring 5" length × 3" diameter and having two 2" × 1¼" windows on the circumference. The can was mounted on 5" diameter discs at both ends. One of the discs also served as the lid for the can. Mounted in the center of the inside of the lid was a fine mesh wire basket, (3" × ¾" diameter) to hold and distribute 2 g of synthetic soil. A hose clamp, 3½" × 4" diamter, was used to secure the carpet samples firmly against the windows. Auxiliary equipment included six ¾" diameter steel balls and a vacuum cleaner.

The soil was applied using the following procedure. Carpet samples (3" × 3½") with finish removed by scour or extraction were padded with 1% by weight solutions of each test fluorochemical to obtain a 100% weight pickup. The padded carpet samples were dried in an oven at 100° C. Approximately 2 g of synthetic soil (dried at 100° C. for 2 hours before use) was placed in the wire basket and the six steel balls were placed in the can. Then the apparatus was assembled and rotated on a ball mill for five minutes in each direction. The ball mill was stopped and the carpet samples were removed. Loose soil was vacuumed off of the surface of the samples using ten strokes in each direction. Soiling was evaluated visually comparing samples with an untreated sample of carpet as a blank. Results of these tests are as follows:

ANIONICS

I (A) — equivalent to untreated sample with little or no soil
I (B) — soiled, no smear
II (A) — heavy soiled, smeared While the invention has been described with reference to certain specific embodiments thereof, it is understood that it is not to be so limited since alterations and changes may be made therein which are within the full intended scope of the appended claims.

What is claimed is:

1. An anionic fluorochemical surfactant selected from the group consisting of:
   (a) a sulfate of 6-hydroxyhexyl perfluoroisopropyl ether,
   (b) a sulfate of a condensation product of one mole of 6-hydroxyhexyl perfluoroisopropyl ether with from about 1 to about 20 moles of ethylene oxide,
   (c) a sulfate of a condensation product of one mole of 2,2,3,4,4,4-hexafluorobutanol with from about 1 to about 5 moles of propylene oxide, and
   (d) a sulfate of a condensation product of one mole of 2,2,3,4,4,4-hexafluorobutanol with from about 1 to about 5 moles of propylene oxide and with from about 1 to about 20 moles of ethylene oxide.

2. The surfactant of claim 1 wherein the surfactant is a sulfate of 6-hydroxyhexyl perfluoroisopropyl ether.

3. The surfactant of claim 1 wherein the surfactant is a sulfate of a condensation product of one mole of 6-hydroxyhexyl perfluoroisopropyl ether with from about 1 to about 20 moles of ethylene oxide.

4. The surfactant of claim 1 wherein the surfactant is a sulfate of a condensation product of one mole of 2,2,3,4,4,4-hexafluorobutanol with from about 1 to about 5 moles of propylene oxide.

5. The surfactant of claim 1 wherein the surfactant is a sulfate of a condensation product of one mole of 2,2,3,4,4,4-hexafluorobutanol with from about 1 to about 5 moles of propylene oxide and with from about 1 to about 20 moles of ethylene oxide.

6. The surfactant of claim 2 selected from the group consisting of monosulfate of 6-hydroxyhexyl perfluoroisopropyl ether and salts thereof.

7. The surfactant of claim 6 wherein the surfactant is the sodium salt of the monosulfate.

8. The surfactant of claim 6 wherein the surfactant is the ammonium salt of the monosulfate.

9. The surfactant of claim 6 wherein the surfactant is the free acid of the monosulfate.

* * * * *